US00PP31676P2

(12) United States Plant Patent
Delabroye

(10) Patent No.: US PP31,676 P2
(45) Date of Patent: Apr. 14, 2020

(54) ***EPIMEDIUM* PLANT NAMED 'MAGNIFICENT'**

(50) Latin Name: ***Epimedium* hybrid**
Varietal Denomination: Magnificent

(71) Applicant: Thierry Delabroye, Hantay (FR)

(72) Inventor: Thierry Delabroye, Hantay (FR)

(73) Assignee: Sandrine DeLaBroye, Hantay (FR)

( * ) Notice: Subject to any disclaimer, the term of this patent is extended or adjusted under 35 U.S.C. 154(b) by 0 days.

(21) Appl. No.: 16/501,174

(22) Filed: Mar. 1, 2019

(30) Foreign Application Priority Data

Jan. 8, 2019 (QZ) ..... PBR 2019/0094

(51) Int. Cl.
*A01H 5/02* (2018.01)
*A01H 6/00* (2018.01)

(52) U.S. Cl.
USPC ..... Plt./429
CPC ..... *A01H 6/00* (2018.05)

(58) Field of Classification Search
USPC ..... Plt./429
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Epimedium* plant, 'Magnificent', that is characterized by its ge similar to plants of the species *Epimedium pinnatum*, its flowers that are conspicuously carried above the foliage, its unique flower coloration with spurred petals that are shorter than the sepals and orange-brown in color and sepals that are pale yellow in color, its flowers that are large in size, its foliage that is dark in color in the winter, its spreading plant shape, and its young leaves that are red-purple in color and change to deep yellow-green as they mature.

3 Drawing Sheets

Botanical classification: *Epimedium* hybrid.
Cultivar designation: 'Magnificent'.

BACKGROUND OF THE INVENTION

The present invention relates to a new and distinct cultivar of *Epimedium* plant of hybrid origin, botanically known as *Epimedium* 'Magnificent' and will be referred to hereafter by its cultivar name, 'Magnificent'.

'Magnificent' originated as a seedling that arose from seed planted from open pollination of an unnamed plant of *E. pinnatum* subsp. *colchicum* by the Inventor in Hantay, France in March of 2011. 'Magnificent' was selected as a single unique plant from the resulting seedlings in spring of 2012.

Asexual propagation of the new cultivar was first accomplished by rhizome division in Hantay, France in September of 2015 by the Inventor. Asexual propagation by rhizome division has determined that the characteristics of the new cultivar are stable and are reproduced true to type in successive generations.

SUMMARY OF THE INVENTION

The following traits have been repeatedly observed and represent the characteristics of 'Magnificent'. These attributes in combination distinguish 'Magnificent' as a new and distinct cultivar of *Epimedium*.

1. 'Magnificent' exhibits foliage similar to plants of the species *Epimedium pinnatum*.
2. 'Magnificent' exhibits flowers that are conspicuously carried above the foliage.

3. 'Magnificent' exhibits a unique flower coloration with spurred petals that are shorter than the sepals and orange-brown in color and sepals that are pale yellow in color.
4. 'Magnificent' exhibits flowers that are large in size.
5. 'Magnificent' exhibits foliage that is dark in color in the winter.
6. 'Magnificent' exhibits a spreading plant shape.
7. 'Magnificent' exhibits young leaves that are red-purple in color and change to deep yellow-green in color as they mature.

The female parent of 'Magnificent' differs from 'Magnificent' in having flowers that are deep yellow in color and mature foliage that is lighter yellow-green in color. 'Magnificent' can be compared to the *Epimedium* cultivars 'Amber Queen' (U.S. Plant Pat. No. 17,197) and 'Fröhnleiten' (not patented). 'Amber Queen' is similar to 'Magnificent' in general flower coloration. 'Amber Queen' differs from 'Magnificent' in having spurred petals that are much longer than the sepals and light yellow in color, sepals that are pale orange in color, and in lacking dark foliage color in winter. 'Fröhnleiten' is similar to 'Magnificent' in winter foliage color. 'Fröhnleiten' differs from 'Magnificent' in having spurred petals that are much shorter and lighter orange-brown in color and in having darker yellow sepals.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BRIEF DESCRIPTION OF THE DRAWINGS

The accompanying colored photographs illustrate the overall appearance and distinct characteristics of the new *Epimedium*. The photographs were taken of a 2.5-year-old plant of 'Magnificent' as field grown in Hantay, France and place in a 33-cm container for the photographs.

The photograph in FIG. 1 provides a side view of 'Magnificent' in bloom.

Figure 1:
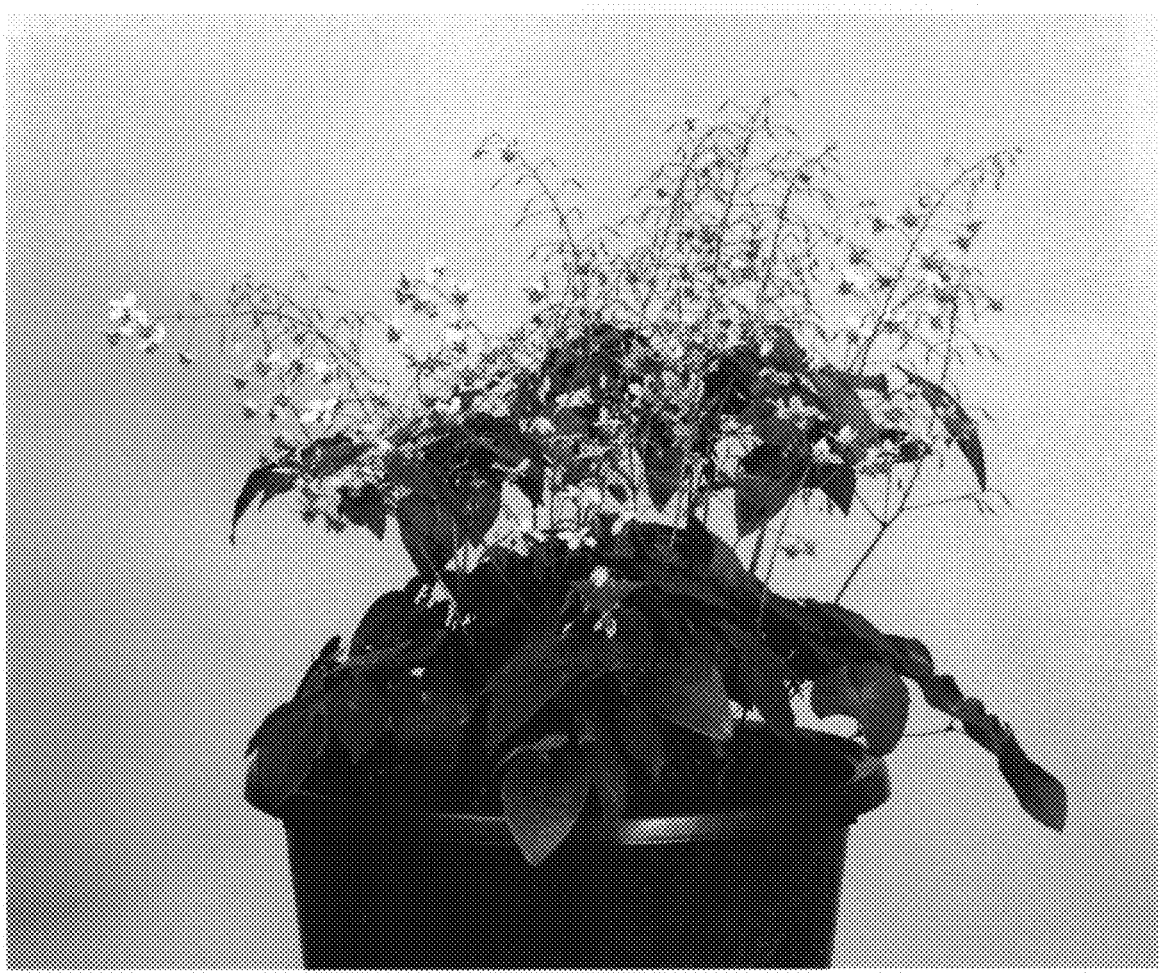
Figure 2:
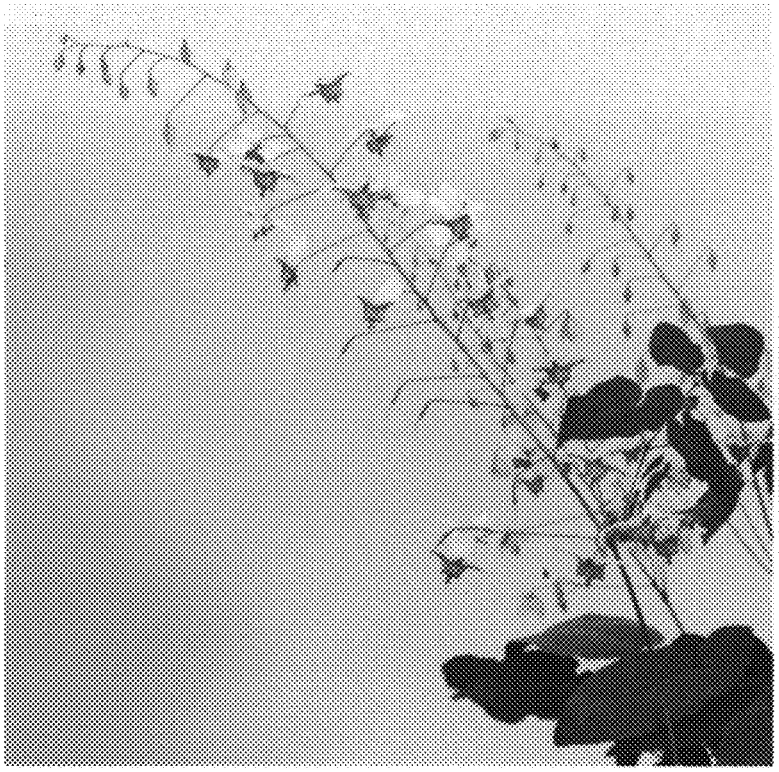

The photograph in FIG. 2 provides a view of an inflorescence of 'Magnificent'.

Figure 3:
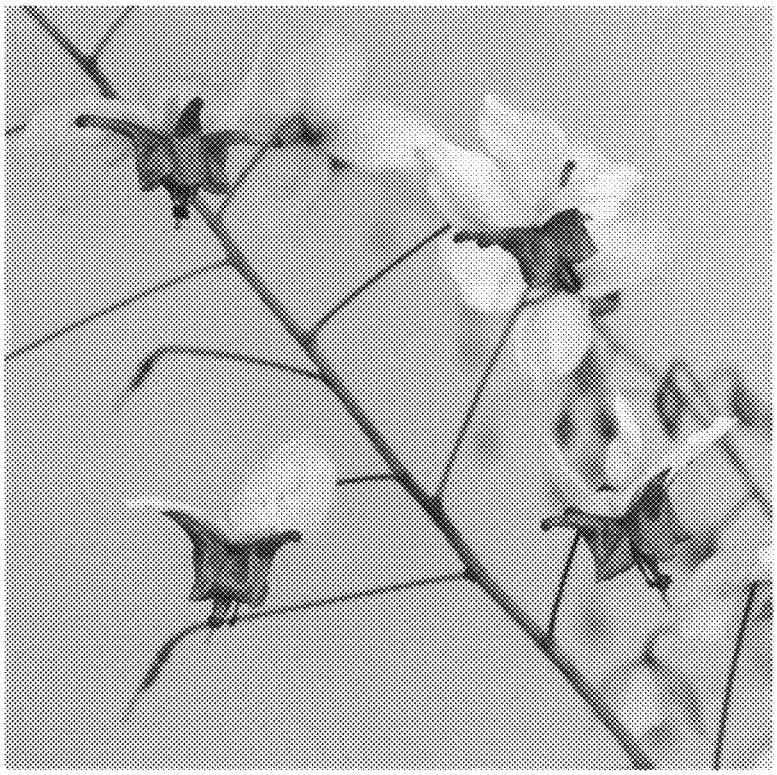

The photograph in FIG. 3 provides a close-up view of the flowers of 'Magnificent'.

Figure 4:
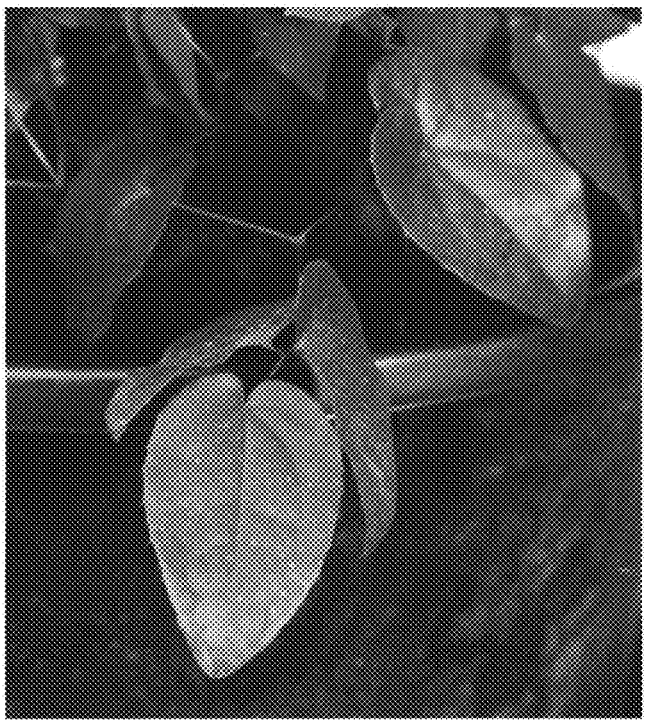

The photograph in FIG. 4 provides a close-up view of the mature foliage of 'Magnificent'.

Figure 5:
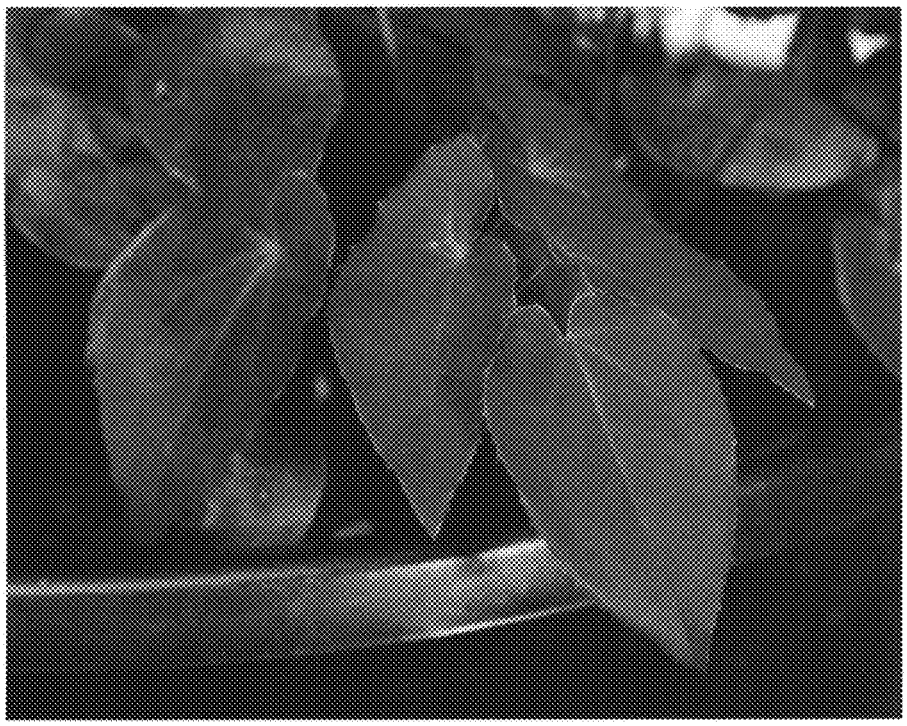

The photograph in FIG. 5 provides a close-up view of the young foliage of 'Magnificent'.

The colors in the photographs are as close as possible with the digital photography and printing techniques utilized and the color codes in the detailed botanical description accurately describe the colors of the new *Epimedium.*

DETAILED BOTANICAL DESCRIPTION OF THE PLANT

The following is a detailed description of 2.5-year-old plants as field grown in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

- *Plant habit.*—Upright, and spreading with semi-long rhizomes.
- *Plant type.*—Herbaceous perennial.
- *Blooming period.*—Average of 6 weeks in spring from March to early May in Hantay, France.
- *Plant height and spread.*—Soil level to top of foliar plane; 30.5 cm, soil level to top of floral plane; 45 cm, plant diameter 51.3 cm.
- *Diseases resistance.*—No susceptibility or resistance to diseases has been observed.
- *Root description.*—Dense, fibrous roots on rhizomes.
- *Rhizomes.*—164A in color, an average of 3.5 cm in length and 5 mm in width with internode length 3 mm, smooth, matte and glabrous surface, average angle of 90° to vertical, strong.
- *Cold hardiness.*—At least in U.S.D.A. Zones 5 to 9.
- *Branching habit.*—Branches arise from rhizome.
- *Propagation.*—Rhizome division.
- *Growth rate.*—Moderate.
- *Root development.*—Time required for root initiation is 6 weeks, time to produce a rooted cutting is 3 months.

Stem description (flowering stem):

- *Stem shape.*—Rounded.
- *Stem size.*—An average of 21 cm in length and 2 mm in diameter.
- *Stem color.*—Young; 151A, mature; N199B.
- *Stem angle.*—An average of 30°.
- *Stem surface.*—Moderately glossy, moderately pubescent with short, very thin hairs that are an average length of 1 mm and too small to measure color.
- *Stem strength.*—Strong.
- *Internode length.*—21 cm.

Foliage description:

- *Leaf division.*—Compound.
- *Leaf size.*—Basal leaf; 16.7 cm in length, 15.8 cm in width, stem leaf; 13.5 cm in length and 10.2 cm in width.
- *Leaflet number.*—Basal leaves 5, stem leaves 3.
- *Leaflet shape.*—Ovate.
- *Leaflet arrangement.*—Opposite.
- *Leaflet margins.*—Serrate with sharp spines.
- *Leaflet size.*—Basal leaf; 8.7 cm in length and 4.3 cm in width, stem leaf; 8.5 cm in length, 5 cm in width.
- *Leaflet apex.*—Acute.
- *Leaflet base.*—Hastate, lobes moderately overlapping.
- *Leaflet surface.*—Both surfaces are smooth, glabrous, slightly rugose, upper surface is moderately glossy, lower surface is matte.
- *Leaflet venation.*—Odd pinnate, upper surface NN137B, lower surface 152B.
- *Leaflet aspect.*—Flat to moderately convexed.
- *Leaflet color.*—Young upper surface; color between N186C and N200A, young lower surface; color between N77A and N187A, mature upper surface; NN137B, mature lower surface; N138B, winter foliage upper and lower surface N186C and tinged N200A.
- *Leaf attachment.*—On petioles that arise from rhizome.
- *Petioles.*—An average of 4.8 cm in length and 1.25 mm in diameter, smooth, glossy, very strong, both surfaces 166A in color.
- *Petiolules.*—An average of 11.8 cm in length and 0.5 mm in diameter, smooth, glossy, very strong, both surfaces 152C in color.

Inflorescence description:

- *Inflorescence type.*—Compound raceme.
- *Inflorescence size.*—Average of 23.7 cm in length, 10.8 cm in diameter.
- *Number of blooms per raceme.*—An average of 50.
- *Flower buds.*—Globose in shape, smooth and glabrous surface, average of 7 mm in length and 3.5 mm in width, 164C and 199B to 199C in color.
- *Flower size.*—An average of 2.7 cm in diameter and 1.2 cm in depth.
- *Flower fragrance.*—None.
- *Lastingness of flowers.*—About 5 days.
- *Sepals.*—4, rotate, 1 whorl, elliptic in shape, attenuate base, acute apex, 1.25 cm in length, 8 mm in width, smooth, glabrous and matte surface, color; when opening upper surface 160D and 161D, base tinged 185B to 185C, veined 185B to 185C, when opening lower surface 161D, base tinged 185B to 185C, veined 185B to 185C, fully open upper surface between 11D and 160D, base tinged 185B to 185C, veined 185C, fully open lower surface between 11C and 160C, base tinged 185B to 185C, veined 185C.
- *Petals.*—4, 1 whorl, 4 mm in length, 3.5 mm in width, base is cuneate, spur portion is 6 mm in length, 1.75 mm in width, broad ovate, strongly concave, petal spurred, spur portion narrow deltoid, broad emarginated to straight, spur portion obtuse, all surfaces are smooth, glabrous and slightly glossy, color; when opening and fully open upper surface 200D, spur part is 199A, base 200D, tip 148A, when fully open upper and lower surface 152D and 161A, base N199D, spur part N199D, tip 197A to 197B.

*Pedicel*.—An average of 2.1 cm in length and 0.4 mm in width, an average angle of 60° to lateral branch axis, strong, 143A to 143B in color, slightly glossy surface, covered with very short glandular hairs average of 0.5 mm in length and too small to measure color.

*Rachis* (*peduncle*).—An average of 21.8 cm in length and 1.5 mm in width, an average angle of 2.5° to lateral branch axis, strong, 143A to 143B in color, slightly glossy surface, covered with very short glandular hairs average of 0.5 mm in length and too small to measure color.

*Androecium*.—Stamens; 8, filaments; 4, 4.5 mm in length, color; 137A, mid-section 138B, base 150B to 150C, anthers; narrow kidney shaped, average of 1 mm in length, 0.4 mm in width, 137A in color, pollen; moderate, 137B in color.

*Gynoecium*.—Pistil; 1, stigma; club-shaped, 0.25 mm in length and diameter, N144A, style; 3.75 mm in length, color; N144A, fading to 181C, ovary; 144B in color.

*Fruit/seeds*.—None observed to date.

It is claimed:

1. A new and distinct cultivar of *Epimedium* plant named 'Magnificent' as herein illustrated and described.

* * * * *